United States Patent
Rhodes

[11] 3,952,412
[45] Apr. 27, 1976

[54] OSCILLATORY SAW

[76] Inventor: William A. Rhodes, 4421 N. 13th Place, Phoenix, Ariz. 85014

[22] Filed: Mar. 28, 1975

[21] Appl. No.: 563,146

[52] U.S. Cl. .............................. 30/166 R; 30/216; 128/317
[51] Int. Cl.² .................... B23D 45/00; B27B 5/29; B26B 19/02; A61B 17/14
[58] Field of Search ................. 30/166 R, 215, 216; 83/602, 782; 128/91 A, 317

[56] References Cited
UNITED STATES PATENTS

| | | | |
|---|---|---|---|
| 909,476 | 1/1909 | Szax | 30/216 X |
| 2,369,925 | 2/1945 | Smith | 30/166 X |
| 2,557,364 | 6/1951 | Treace | 128/317 |
| 2,702,550 | 2/1955 | Rowe | 128/317 |
| 3,852,881 | 12/1974 | Treace | 128/317 X |
| 3,857,177 | 12/1974 | Karubiam et al. | 30/216 |

Primary Examiner—Channing L. Pace

[57] ABSTRACT

An oscillatory saw wherein a motor is provided with an output shaft driving a multi-lobe cam having an uneven number of cam lobes in excess of two and wherein a pair of opposed cam followers engage the multi-lobe cam in such a manner that one of the followers may be adjacent to a lobe of the cam while the opposite cam follower bearing may be adjacent to an area of the cam between a pair of the cam lobes thereby providing for oscillatory motion of the cam followers and the saw blade connected thereto. The disclosure also relating to a novel arrangement of a cam follower yoke having opposed cam follower bearings and a saw blade pivoted on a common pivot with the yoke and having an arcuate row of openings into which a trunnion of the yoke fits so as to drive the blade. The disclosure also relating to means on the yoke for engaging teeth at the periphery of the blade for driving it. The disclosure also related to multi-lobe cams having an uneven number of lobes in accordance with the foregoing comprising cams having three, five and seven lobes respectively.

The disclosure being related specifically to oscillatory saws which are small, compact and operated at very high frequency and which are particularly adapted for use as cast cutters, bone saws and similar uses.

14 Claims, 6 Drawing Figures

U.S. Patent    April 27, 1976    3,952,412
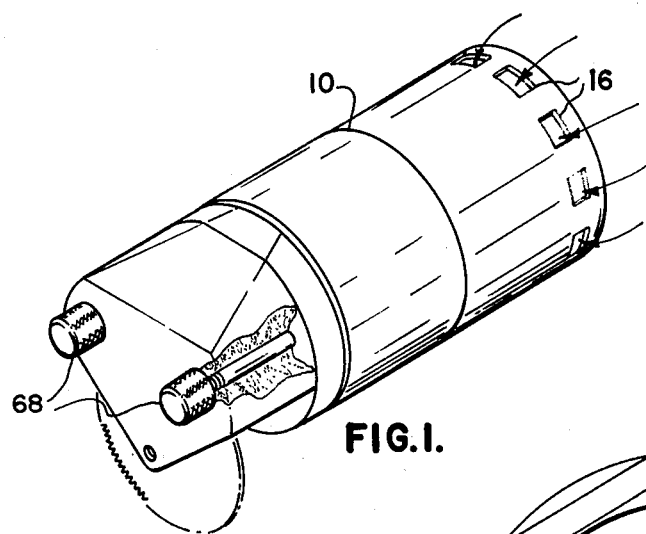
FIG.1.
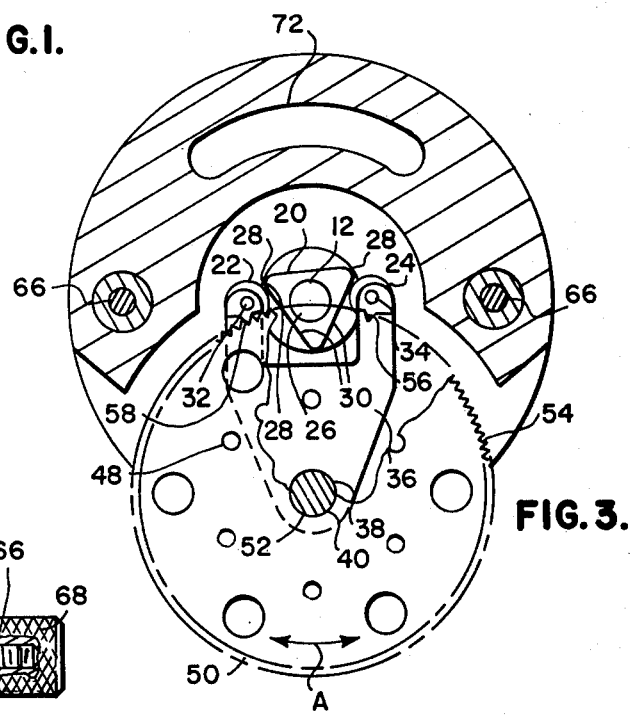
FIG.3.
FIG.2.
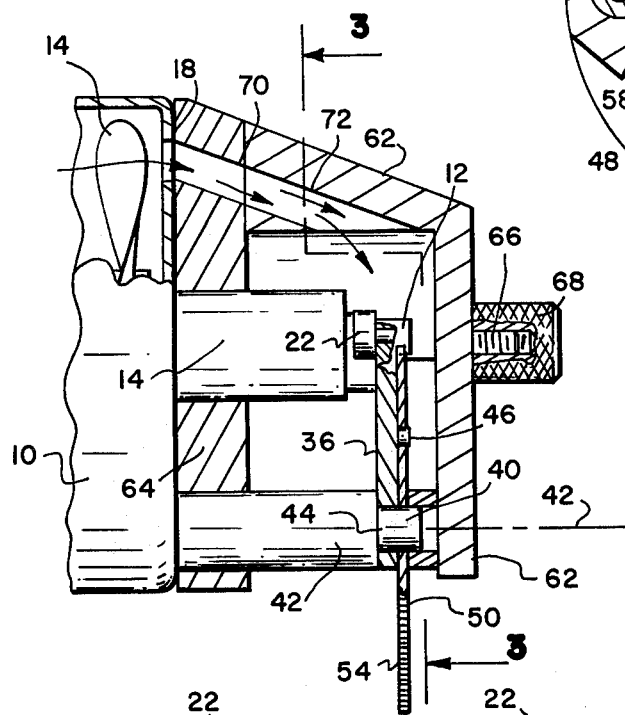
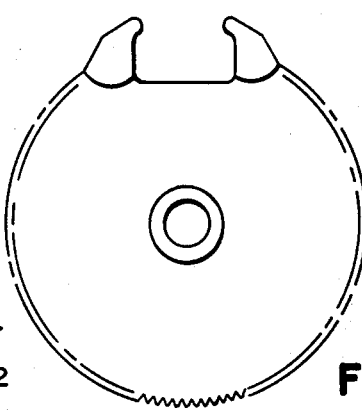
FIG.4.
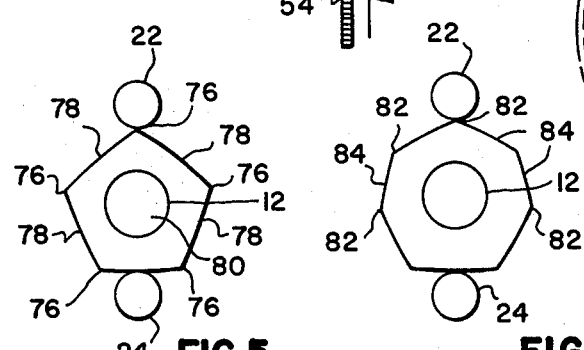
FIG.5.    FIG.6.

OSCILLATORY SAW

PRIOR ART

The following prior art is hereby made a record in this application.

| UNITED STATES PATENTS |
| --- |
| 1,945,247 |
| 2,557,364 |
| 2,702,550 |
| GERMAN PATENT |
| 719,969 |

BACKGROUND OF THE INVENTION

The foregoing prior art patents relate generally to oscillatory saws but none of them utilize multi-lobe cams having an uneven number of lobes in excess of two and where opposed cam follower bearings engage concurrently a lobe and an area of the cam intermediate pair of lobes. The prior art being related to relatively complicated structures as well as those which are of relatively low oscillatory frequency when in operation and consequently the prior art devices are relatively bulky as compared to that of the present invention. Many of the prior art structures involve a pair of blades serving generally in a manner of a clipper arrangement, the blades being operable in opposite directions by separate single lobe cams disposed 180° relative to each other.

SUMMARY OF THE INVENTION

The present invention relates to a very compact oscillatory saw particularly adapted for use in surgical work for cutting bones or for cutting casts from the limbs of a person after having had a bone set and healed. The oscillatory saw of the invention having means for very high frequency oscillatory motion of the saw and consequently the overall size of the entire saw including the motor is very small and compact. The saw being provided with a motor driving a cam directly on its output shaft and rotating at high speed. The cam being a multi-lobe cam having an uneven number of cam lobes in excess of two, the uneven number being such that one lobe may engage one of a pair of opposed cam followers while the opposite cam follower is engaged by the cam between a pair of lobes. The uneven number of lobes may be three, five or seven, for example, and these configurations are such that when the cam follower bearings are disposed in 180° apart about the axis of the cam that one follower will be on a relatively flat area of the cam while the other follower may be engaged by a projecting point like lobe of the cam. Accordingly, the motor shaft operating at high speed and with at least three lobes on the cam, the oscillatory frequency of the saw moved by the cam follower bearings is very high so as to provide very efficient and rapid cutting action with a relatively small compact high speed unit.

The oscillatory saw of the invention comprises a novel arrangement of a cam follower yoke having a pair of cam follower bearings opposed to each other and located substantially 180° apart with respect to the axis of the cam. The cam follower yoke being pivotably mounted on a pivot bearing which is a pivot bearing for the saw blade and the saw blade is provided with a row of arcuate teeth concentric with the pivot bearing. Additionally, the invention comprises a novel means of carrying the saw blade on the yoke whereby the saw blade is centrally pivoted on the aforementioned pivot bearing and the saw blade is also provided with an arcuate row of openings adapted to be engaged over a projecting trunnion on the yoke.

Additionally, the yoke is provided with a pair of teeth engaging portions adapted to engage the teeth of the periphery of a circular configuration of the saw blade.

Furthermore, the invention comprises novel means for ventilating the cam and cam followers of the structure whereby the motor driving a fan moves air over the cam and the cam followers and forces the air to move in a direction to carry dust away from the area of the cam thereby alleviating the possibility that dust caused by operation of the saw will cause a frictional problem in the area of the high speed cam and its cam followers.

Additionally, the invention comprises a novel frame coupled directly to the end of a motor housing and the frame comprises a removable cap which is readily and easily removed by a thumb screw so as to allow the saw and the cam follower yoke to be removed axially from the end of the saw and yoke pivot bearing which is axially parallel to the rotary axis of the motor shaft and the cam.

Accordingly, it is an object of the invention to provide a compact high speed oscillatory saw for cast cutting and surgery practice and for other uses which become apparent.

Another object of the invention is to provide a novel oscillatory saw having a motor powered cam provided with an uneven number of lobes in excess of two and a saw operable by a pair of cam follower bearings opposed to each other and 180° apart relative to the axis of the cam such that one of the cam follower bearings may be adjacent to a lobe or point area of the cam while the other of the cam follower bearings may be at an area of the cam intermediate a pair of said lobes.

Another object of the invention is to provide a means of the foregoing features wherein the cam may employ an uneven number of lobes such as three lobes, five lobes or seven lobes by way of example.

Another object of the invention is to provide a novel arrangement of a motor housing and a frame having a removable cap which is adapted for removal to replace saw blades and cam follower yokes and/or cams such that when the cap is removed the cam follower and blade mechanism may be axially removed from a simple pivot bearing.

Another object of the invention is to provide a novel means of motor cooling and air flow venting of the area of the cam and cam followers such as to cool these mechanisms and also to provide air flow for preventing dust from the saw to be carried into the area of the cam and cam followers to thereby keep them clean and to alleviate friction.

Other objects and advantages of the invention may be apparent from the following specification, appended claims and accompanying drawings.

BRIEF DESCRIPTION OF THE DRAWINGS

FIG. 1 is a perspective view of an oscillatory saw in accordance with the present invention;

FIG. 2 is a fragmentary axial sectional view of a portion of the motor and housing and of the frame and oscillatory mechanism showing some of the parts in elevation and portions broken away and in section to amplify the illustration;

FIG. 3 is a sectional view taken from the line 3—3 of FIG. 2 showing parts and portions in elevation and portions broken away to amplify the illustration;

FIG. 4 is a view of a modified form of the invention wherein the cam follower bearings are fixed to the saw blade;

FIG. 5 is a diagrammatic view showing a pair of cam follower bearings and a five lobe cam; and FIG. 6 is a diagrammatic view showing a pair of cam followers and a seven lobe cam.

DESCRIPTION OF THE PREFERRED EMBODIMENTS

The oscillatory saw of the invention is provided with a motor contained in a housing 10. The motor is provided with an output shaft 12 which rotates in a cylindrical extension 14 wherein a suitable bearing provides for accurate concentric rotative guidance of the shaft 12. Inside the housing 10 mounted on the shaft 12 is a ventilating fan 14 which moves air into openings 16 in the housing 10 and vents air out through an opening 18 and into the frame area of the invention as will be hereinafter described in detail.

Mounted on the shaft 12 is a multi-lobe cam 20 shown best in FIG. 3 of the drawings. This multi-lobe cam 20 has an uneven number of cam lobes in excess of two. The particular cam as shown in FIG. 3 by way of example is a preferred form of the invention and has three lobes which are disposed between a pair of cam follower bearings 22 and 24 and these bearings are disposed 180° apart about the axis 26 of the shaft 12 and cam 20.

It will be seen that the cam 20 is provided with lobe portions 28. These portions 28 are relatively pointed but slightly rounded off and the cam is also provided with intermediate portions 30 between the lobes 28 and these intermediate portions 30 are relatively flat although are usually slightly convex to conform with the usual rotating geometry related to the cam follower bearings 22 and 24 depending upon the relative diameters of these bearings as well as the radius of the cam 20 to its lobe areas 28 as well as its intermediate portions 30.

The dimensions of the cam are such that one of the lobes 28 may be engaged with one of the cam follower bearings 24 while a relatively intermediate portion 30 between the lobes may be engaged with the other of the cam follower bearings.

The cam follower bearings shown in FIG. 3 are roller bearings mounted on respective shafts 32 and 34 carried by a yoke 36. This yoke 36 having a bearing opening 38 which is pivotably mounted on a saw pivot bearing 40 which is provided with a central axis 42 as shown in FIG. 2 of the drawings. This axis 42 being substantially parallel with the rotating axis of the motor shaft 12.

As shown in FIG. 2 of the drawings, the saw pivot bearing 40 is provided with an enlarged portion 42 having a shoulder 44 adjacent to which the yoke 36 is disposed. The yoke 36 is provided with a driving trunnion 46 which is engaged in one of a plurality of openings 48 in a circular saw blade 50. The openings 48 being concentric with a center bearing area of the saw blade designated 52 and this bearing area 52 is an opening through the center of the saw blade adapted to oscillate around the saw pivot bearing 40.

The trunnion 46 may be disposed in any one of a plurality of openings 48 in the saw blade which are arranged in an arcuate row outwardly of the pivotal axis of the blade.

The saw blade 50 is provided with an arcuate row of cutting teeth 54 around the periphery thereof and the yoke is provided with a pair of nibs 56 and 58 which also engage the teeth 54 so as to provide a driving media for the saw blade outwards of the rotating axis.

The various openings 48 and teeth 54 may be disposed in various positions relative to the trunnion 46 and the nibs 56 and 58 so that various areas of the periphery of the blade may be disposed in the area A as some of the teeth wear and thus the periphery of the blade may be shifted so as to utilize all of the teeth around the entire periphery before the blade is discarded.

The saw blade 50 is engaged by a spacer 60 which surrounds the saw blade pivot bearing 40. This spacer is held adjacent the blade 50 by means of a housing cap 62 which is secured to a frame plate 64 on the end of the motor housing 10. This frame plate 64 is fixed to the motor housing 10 and the cap 62 is secured to the motor housing 10 by screws 66 on which thumb nuts 68 are disposed to bear against the cap and hold it onto the plate 64.

The fan 14 discharges air through an opening 70 in the plate 64 and communicating with the opening 70 is a similar opening 72 in the cap 62. The opening 72 being shown in FIGS. 2 and 3 of the drawings and communicating with an inside area of the cap adjacent to the cam 20 and the cam followers 22 and 24.

When the motor is operating the fan 14 forces air as indicated by the arrows into the area of the cam and the cam followers and in a direction toward the saw blade 50 so as to force air to travel away from the cam and the followers and to prevent dust from the oscillating saw 50 from flowing into the area of the cam and the cam followers.

It will be seen that FIGS. 5 and 6 disclose cams having five and seven lobes respectively. The lobes of the cam as shown in FIG. 5 are designated 76 and the intermediate portions between the lobes are designated 78. It will be seen that the cam followers 22 and 24 are disposed 180° relative to the axis 80 of the shaft 12. Accordingly, one of the cam follower bearings 22 or 24 engages a lobe or point on the cam while the other opposed cam follower bearing engages a relatively flat portion or an intermediate area between the lobes 76. FIG. 6 disclosing the seven lobe cam illustrates a cam wherein the lobes are designated 82 and the intermediate portions are designated 84 and function in a similar manner with respect to that disclosed in connection with FIG. 5 of the drawings.

It will be obvious to those skilled in the art that various modifications may be resorted to without departing from the spirit of the invention.

I claim:

1. In an oscillatory saw; a frame; a motor fixed to said frame; said motor having a rotary output shaft; a multi-lobe cam having an uneven number of lobes in excess of two; said cam fixed on said shaft; a blade pivot bearing fixed on said frame; said blade pivot bearing being generally laterally spaced and axially parallel to said rotary output shaft of said motor; a yoke pivoted on said pivot bearing; a blade carried by said yoke; said blade having an arcuate row of cutting teeth concentric with said pivot bearing; said yoke having a pair of opposed cam follower bearings disposed to straddle said multi-lobe cam such that one of said cam follower bearings may be engaged by one of said lobes while the opposed cam follower bearing is disposed at an area of said cam which is intermediate two of said lobes of said cam; said yoke thus disposed to be oscillated about said pivot bearing; said blade coupled to said yoke for unison oscillatory operation therewith about the axis of said blade pivot bearing.

2. The invention as defined in claim 1, wherein: said blade is circular with a central opening disposed around said blade pivot bearing; said blade also having an arcuate row of openings disposed outwardly of the center thereof; said yoke having a trunnion adapted to be engaged in any one of said last mentioned openings in said arcuate row.

3. The invention as defined in claim 1, wherein: said cam follower bearings carried by said yoke are roller type cam followers.

4. The invention as defined in claim 3, wherein: said blade is circular and having a central opening pivotable about said blade pivot bearing; said blade also having an arcuate row of openings therein spaced from the center thereof; said yoke having a trunnion adapted to be engaged in any one of said openings of said arcuate row so as to provide for adjustment of the periphery of said blade to compensate for wear of any of the teeth on various portions of the periphery.

5. The invention as defined in claim 1, wherein: said frame is provided with a removable cap having retainer means for holding said blade and said yoke on said blade pivot bearing and whereby said cap when removed allows said blade and said yoke to be removed axially from the end of said blade pivot bearing and from an area wherein said cam follower bearings are disposed at opposite sides of said cam.

6. The invention as defined in claim 5, wherein: said motor is provided with a conventional housing and said frame is secured to one end of said motor comprising a mounting plate secured to one end of said motor and said cap being removably secured to said mounting plate.

7. The invention as defined in claim 6, wherein: said blade is circular and having an annular row of cutting teeth on its periphery and said blade provided with a central opening pivoted on said blade pivot bearing; said blade also having an arcuate row of openings disposed outwardly from the center thereof; said yoke having a trunnion engageable in any one of said openings of said arcuate row in said blade.

8. In an oscillatory saw; a frame; a motor fixed to said frame; said motor having a rotary output shaft; a multi-lobe cam having an uneven number of lobes in excess of two; said cam fixed on said shaft; a blade pivot bearing fixed on said frame; said blade pivot bearing being laterally spaced and generally axially parallel to said rotary output shaft of said motor; a blade pivoted on said pivot bearing and having an arcuate row of cutting teeth concentric with said pivot bearing; said blade having a pair of opposed cam follower bearings disposed to straddle said multi-lobe cam such that one of said cam follower bearings may be engaged by one of said lobes while the opposed cam follower bearing is disposed at one area of said cam which is intermediate two of said lobes of said cam; said yoke thus disposed to be oscillated about said pivot bearing; said blade coupled to said yoke for unison oscillatory operation therewith.

9. The invention as defined in claim 1, wherein: said cam is provided with three lobes.

10. The invention as defined in claim 1, wherein: said cam is provided with five lobes.

11. The invention as defined in claim 1, wherein: said cam is provided with seven lobes.

12. The invention as defined in claim 1, wherein: said blade is circular and having an annular row of teeth around its periphery; said yoke having means engaging said teeth for holding said blade in fixed position relative to said yoke as it oscillates around said blade pivot bearing.

13. The invention as defined in claim 1, wherein: said motor is provided with a housing having air inlets at one end and air outlets at the other end; a fan in said housing operable by said motor; said fan disposed to force air toward said frame; openings passing from said fan and into the area of said frame around said cam; whereby air cools said motor and forces air into an area of said frame and said cam for cooling said cam and said cam follower bearings.

14. The invention as defined in claim 13, wherein: said frame having cap means adapted to direct the air toward said cam and in a direction toward the cutting area of said blade so as to force dust and cuttings away from said cam follower and said cam follower bearings.

* * * * *